United States Patent [19]

Masuda et al.

[11] Patent Number: 4,875,758
[45] Date of Patent: Oct. 24, 1989

[54] PLASTIC-COATED OPTICAL TRANSMISSION FIBER AND AN ESTIMATING METHOD THEREOF

[75] Inventors: Shigeo Masuda; Toshifumi Hosoya, both of Kanagawa, Japan

[73] Assignee: Sumitomo Electric Industries, Ltd., Osaka, Japan

[21] Appl. No.: 291,292

[22] Filed: Dec. 28, 1988

[30] Foreign Application Priority Data

Dec. 28, 1987 [JP] Japan .............................. 62-334265
Jan. 8, 1988 [JP] Japan .................................. 63-3021

[51] Int. Cl.⁴ ............................................. G02B 5/172
[52] U.S. Cl. ................................ 350/96.30; 350/96.34
[58] Field of Search ............... 350/96.29, 96.30, 96.31, 350/96.33, 96.34

[56] References Cited

U.S. PATENT DOCUMENTS

| | | | |
|---|---|---|---|
| 4,209,229 | 6/1980 | Rittler | 350/96.30 X |
| 4,521,073 | 6/1985 | Murakami et al. | 350/96.34 |
| 4,660,928 | 4/1987 | Jaeger et al. | 350/96.30 |
| 4,756,599 | 7/1988 | Maeda et al. | 350/96.34 X |
| 4,783,135 | 11/1988 | Utsumi et al. | 350/96.34 X |
| 4,804,259 | 2/1989 | Sasaki et al. | 350/96.34 X |
| 4,812,011 | 3/1989 | Tatsukami et al. | 350/96.34 |

*Primary Examiner*—William L. Sikes
*Assistant Examiner*—Akm E. Ullah
*Attorney, Agent, or Firm*—Cushman, Darby & Cushman

[57] ABSTRACT

Optical-transmission fibers serve to transmit signal over some distance. Said fibers have traditionally been constructed of a glass fiber; consisting of a central core and an outside clad, a surrounding soft layer around said fiber and a hard layer around the soft layer. Because of the material construction, said fibers had high dynamic losses. By altering the materials used around the glass fiber, the present invention has successfully dramatically reduced the dynamic loss and therefore greatly improved the possibilities for signal transmission. The organic material used to enhance transmission ability may vary but the effect is such that the dynamic loss remains low as compared to any previous art.

5 Claims, 2 Drawing Sheets

| MEASUREMENT | | COMP. EXAMP. 1 | COMP. EXAMP. 2 | COMP. EXAMP. 3 | EMB. 1 | EMB. 2 | EMB. 3 |
|---|---|---|---|---|---|---|---|
| | OUTER DIAMETER OF GLASS FIBER (mm) | 0.125 | 0.125 | 0.125 | 0.125 | 0.125 | 0.125 |
| | DIAMETER OF SOFT LAYER (mm) | 0.200 | 0.190 | 0.200 | 0.200 | 0.190 | 0.200 |
| | DIAMETER OF HARD LAYER (mm) | 0.600 | 0.250 | 0.600 | 0.600 | 0.250 | 0.600 |
| TRANSMISSION CHARACTER- ISTICS | INITIAL CHARACTERISTICS (dB/km) | 0.36 | 0.35 | 0.58 | 0.33 | 0.33 | 0.55 |
| | TEMPERATURE CHARACTERISTICS (ΔdB/km, −40°C) | +0.5 | +0.5 | +0.4 | ±0.0 | ±0.0 | ±0.0 |

PLASTIC-COATED OPTICAL TRANSMISSION FIBER AND AN ESTIMATING METHOD THEREOF

BACKGROUND OF THE INVENTION

The present invention relates to a plastic-coated optical transmission fiber in which a glass fiber is coated with an organic matter. More specifically, this invention relates to a more effective means of transmission due to said coating.

Recently, demand for long-distance optical communication has increased and further improvement in transmission characteristics of optical fiber transmission line is desirable. Conventional optical transmission fibers and the conventional method for estimating the tightness between the glass fiber and its coating have become insufficient to meet current demand.

The particular type of coating material used in an optical fiber transmission line influences its transmission characteristics. It has been reported that when temperature changes over a wide range, the shrinking and expanding of the coating material cause a microbending of the glass fiber and thereby causes a deterioration of transmission characteristics.

It has been difficult to obtain using standard production methods optical transmission fibers superior in transmission characteristics with good reproducibility over a wide temperature range on the basis of only the theoretically calculated forces resulting from shrinking or expanding of the coating material. Further, it has been difficult to estimate accurately the tightness between the glass fibers and the coatings.

Accordingly, there has been investigation of the influence on transmission characteristics of the tightness between the coating material and glass fiber and how to estimate that tightness.

In a conventional method of estimating tightness, the "drawing" force with which a glass fiber is pulled out of an optical transmission fiber is measured so as to determine "fastening" force with which the coating material fastens to the glass fiber. Tightness can also be estimated from the quantity of shrinkage of the coating material on the basis of a heat-cycle test in a temperature range from a low temperature to a high temperature (for example, from $-40°$ C. to $+60°$ C.).

However, in practice, even in cases where it was estimated that the degree of tightness should be suitable in accordance with conventional estimating methods, abnormality often occurred in transmission loss when an optical transmission fiber was used at low or high temperatures.

Accordingly, it has been desired to develop an optical transmission fiber and an estimation method, in which a glass fiber and a coating material are fabricated so as to be in close contact with each other in a manner providing a good transmission characteristic over a wide temperature range.

Optical fibers for communication are formed in a manner so that a glass base material (preform) is spun and then coated with a macro molecular material. A generally-used optical transmission fiber, made from a glass fiber of silica glass, fluoride glass, or the like, has both a central core and an outside clad. The glass fiber, both the core and the clad, is coated with a soft layer. The outside of the glass fiber coated with the soft layer is further coated with a hard layer so as to form an optical transmission fiber having a single core.

The soft layer acts as a cushion against the glass fiber and is made of a soft resin. Specifically, the soft resin may be thermosetting silicone, ultraviolet (hereinafter abbreviated to "UV") curable silicone, UV curable urethane acrylate, UV setting epoxy acrylate, UV setting ester acrylate, or the like. The hard outside layer protects the glass fiber from the outside of the soft layer and is made of a stiff resin. The stiff resin may be extrusion resin such as polyamide, polyester, ABS resin, polyacetal resin, or the like, or any kind of UV curable resin. Those coating materials are often used in the colored state. When used in such a manner, either or both of the materials for the soft layer and the hard layer is colored. Sometimes, a colored layer is provided outside the hard layer or is interposed between the soft layer and the hard layer.

Investigation has shown that the conventional coating materials have been used in various combinations. That is, for the soft layer, generally a material is used that has a glass transition temperature lower than $-50°$ C. and a Young's modulus lower than $0.5$ $Kg/mm^2$ at ordinary temperatures. For the hard layer a material is generally used that has a glass transition temperature higher than an ordinary temperature ($0° \sim 20°$ C.) and a Young's modulus higher than $30$ $Kg/mm^2$ at ordinary temperatures. By variously combining those materials, it is possible to improve the transmission characteristics.

SUMMARY OF THE INVENTION

According to the present invention there is provided an improved optical transmission line and method for estimating tightness between a glass fiber and a coating material.

If dynamic vibrations are applied to an optical transmission fiber at one end and stress is detected at its other end, elastic transformation and viscosity flow appear dynamically in superposition, so that the dynamic viscoelasticity can be measured. As a result of an investigation on the temperature characteristic of the dynamic viscoelasticity, it has been found that the temperature characteristic reflects the tightness between a glass fiber and a coating material. Accordingly, when a glass fiber and an organic coating material in an optical transmission fiber are made to be in close contact with each other to an extent that the lower limit of temperature at which the dynamic loss (tan δ) obtained by measuring the dynamic viscoelasticity begins to indicate $0.05$ or more is not higher than $60°$ C., the optical transmission fiber has a superior transmission characteristic over a wide temperature range.

Further, according to the present invention, the optical transmission fiber having a superior transmission characteristic over a wide temperature range can accurately be estimated by estimating the tightness between the coating material and the glass fiber based upon a relationship between the dynamic loss and the temperature.

It is an object of the present invention to provide a novel plastic-coated optical transmission fiber having an extremely good transmission characteristic over a wide temperature range.

It is another object of the present invention to provide a method for accurately estimating whether or not a plastic-coated optical transmission fiber will have good transmission characteristic over a wide tempera-

BRIEF DESCRIPTION OF THE DRAWINGS

The invention will be described in greater detail with reference to the drawings, wherein.

DETAILED DESCRIPTION OF PREFERRED EMBODIMENTS

Accordingly to the present invention, there is provided a plastic-coated optical transmission fiber and a method for estimating the tightness of that transmission fiber. The fiber's transmission characteristic is good over a wide temperature range and the optical transmission characteristic can be accurately estimated.

Figure 1:
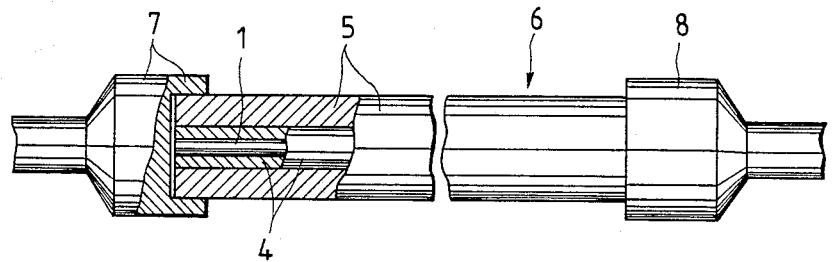
FIG. 1 is of an arrangement for an arrangement for measuring the viscoelasticity of an optical transmission fiber.

In order to measure an optical transmission fiber, it is cut to a suitable length and the dynamic viscoelasticity is measured in accordance with the arrangement shown in FIG. 1. Dynamic vibrations are applied to the optical transmission fiber at one end and stress is detected at the other end to thereby obtain a dynamic loss (tan δ). In general material arrangements in optical transmission fibers, the Young's modulus of a glass fiber is about 7000 kg/mm². Because the Young's modulus of a glass fiber is large, about 200 times or more that of a hard layer, the dynamic loss (tan δ) due to molecular movement in the soft and hard layers is small in the measurement of the dynamic viscoelasticity.

Figure 2:
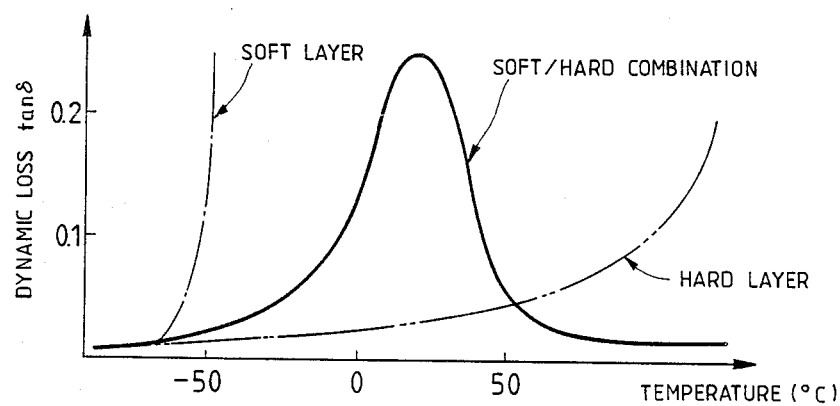
FIG. 2 is a graph of the dynamic viscoelasticity of just a soft layer, just a hard layer, and a soft/hard combination.
Figure 5:
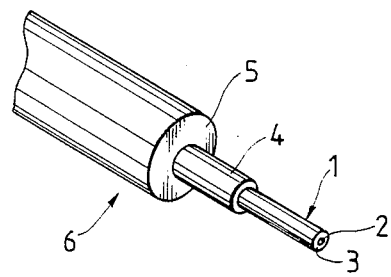
FIG. 5 is a perspective view of a typical optical-transmission fiber where the parts are defined as follows: 1-glass fiber, 2-central core, 3-outside clad, 4-soft layer, 5-hard layer, and 6-entire optical-transmission fiber.

If the dynamic viscoelasticity is measured as described above, however, a behavior different from that due to the molecular movement in soft and hard layers appears as indicated by a solid line in FIG. 2. In the drawing, a one-dotted chain line indicates a case where only a soft layer is provided, a two-dotted line indicates a case where only a hard layer provided, and the solid line indicates a case where soft and hard layers are provided in an optical transmission fiber. The behavior of the dynamic viscoelasticity of the optical transmission fiber reflects the tightness between the glass fiber and the coating material. Accordingly, if the above-mentioned tightness is estimated in the measurement of dynamic viscoelasticity and established to such an extent as described above, it is possible to obtain and estimate a plastic-coated optical transmission fiber in which no microbending due to shrinking force of a coating material occurs over a wide temperature range, and which is novel, useful and superior in transmission characteristic.

Specific embodiments of the invention will now be described. The same elements are referenced correspondingly and repeated description will be omitted.

As stated, FIG. 1 shows an arrangement for measuring dynamic viscoelasticity for estimating the degree of tightness between glass fibers and coating materials in realizing the optical transmission fibers according to the present invention. An optical transmission fiber 6 cut in a fixed length, is held at one end by a vibration chuck 7 and at its other end by a detection chuck 8. Vibration chuck 7 is arranged to apply dynamic vibrations to optical transmission fiber 6 and detection chuck 8 is arranged to detect stress of transmission fiber 6. The dynamic viscoelasticity is measured on the basis of the detected stress so as to obtain a dynamic loss (tan δ).

Such a measuring method has been used in measuring dynamic viscoelastic behavior of a macromolecular material. Information is obtained as to cohesion of molecules such as a glass transition temperature, fusion/crystallinity, crosslinking phase separation, etc. Accordingly, by measuring the dynamic viscoelasticity of the coating materials remained after the glass fiber has removed from the optical transmission fiber, it is possible to obtain useful data such as identification, heat-resistance, a thickness ratio of coatings, and so on, of the materials. Further, the measurement has been used for estimation of the degree of curing of an insulating coating as disclosed, for example, in Japanese Publication No. 54-17184.

According to the present invention, such a method of measuring dynamic viscoelasticity is applied to the estimation per se of the tightness of an optical transmission fiber. That is, if the dynamic viscoelasticity of an optical transmission fiber set as shown in FIG. 1 is measured, a behavior due to the tightness between the glass fiber and the coating materials appears as indicated by a solid line in FIG. 2. Further, a temperature characteristic of the dynamic viscoelasticity is obtained under variations in the tightness between the glass fiber and the soft layer of the coatings. Then, the temperature characteristics of the dynamic loss (tan δ) can be obtained as shown in FIG. 3.

Figures 3, 4:
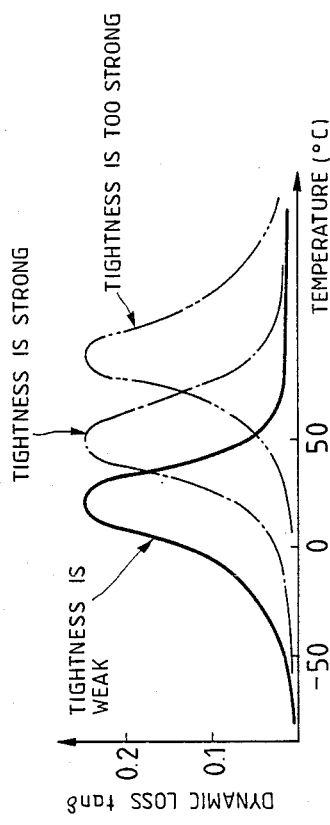
FIG. 3 is a graph of the temperature characteristic for a weak, strong, and much too strong tightness.
FIG. 4 shows specific examples of the present invention and of comparative examples.

In FIG. 3, a solid line indicates the case of weak tightness, an one-dotted chain line indicates the case of strong tightness, and a two-dotted chain line indicates the case of extremely strong tightness. As seen from the drawing, the weaker the tightness, the lower the lower limit of the temperature from which the dynamic loss (tan δ) is generated, while the stronger the tightness, the higher the lower limit of the temperature from which the dynamic loss (tan δ) is generated. The tightness between the glass fiber and the coating materials can be grasped quantitatively above a temperature at which the dynamic loss (tan δ) is equal to a predetermined value (0.05 or more, for example) or above a temperature at which the curve shown in FIG. 3 indicates a peak not smaller than 0.05.

Even in the composite materials, for example, for an optical transmission fiber, which are extremely different in Young's modulus from each other, in the case where the ratio occupied by a high elastic material is small, that is, in the case where the ratio of the sectional area of glass fiber to the whole sectional area of an optical transmission fiber is smaller than about 50%, the dynamic energy consumption varies depending on the degree of the tightness and it comes out as a dynamic loss (tan δ). The energy consumption is small in the case where the tightness on the interface is extremely strong or extremely weak, however, the consumption becomes gradually large as the tightness begins to become gradually weak due to the rise of a temperature or the like. That is, on the temperature characteristic curve of the dynamic loss (tan δ) the value of tan δ becomes large. This fact indicates that the weaker the tightness, the smaller the lower limit of the temperature above which the dynamic loss (tan δ) begins to become large, while the stronger the tightness the higher the lower limit of the temperature above which the dynamic loss (tan δ) begins to become large. Further, this fact indicates that the resonance due to dynamic vibration depends on the degree of the tightness between the glass fiber and the coating materials.

On the basis of such knowledge, there has been developed an estimating method for estimating accurately a plastic-coated optical transmission fiber having such a characteristic that the lower limit of temperature at which the dynamic loss (tan δ) due to resonance begins to rise (the temperature at which the dynamic loss becomes 0.05 or more) is lower than, for example, about 60° C., the optical transmission fiber being improved so that the transmission characteristic is superior over a wide temperature range. That is, it is considered that if the lower limit of temperature at which the dynamic loss (tan δ) begins to rise is higher than about 60° C., the shrinking force of the coating materials becomes so large at a lower temperature that microbending is caused in the glass fiber. On the other hand, it is considered that if the lower limit of temperature at which the dynamic loss (tan δ) begins to rise to 0.05 or more is low, for example, about 20° C., the shrinking force of the coating materials at a lower temperature is too small to cause microbending which may make the transmissions loss of the glass fiber large.

The degree of tightness between the glass fiber and the coating materials can be set through various methods. For example, when silicon resin is used for the soft layer, the tightness may be set only by changing the concentration of OH-radicals in the silicone resin. That is, larger the concentration of OH-radicals, the stronger the tightness between the glass fibers and the silicon resin becomes. Further, when any other material than silicon resin is used for the soft layer. For example, it will do to add a silane coupling agent to the material.

Referring to FIG. 4, the specific examples of the present invention and comparative examples are described hereunder.

In the experiment, LS-3380, made by SHZN-ETSU CHEMICAL INDUSTRY was used as the silane coupling agent for controlling tightness, and RHEOVIBRON made by ORIENTECH Co., Ltd., was used as a dynamic viscoelasticity measuring device with measuring conditions in which the frequency of dynamic vibration was 11 Hertz, and the rate of temperature rising was 3° C./minute. For the measurement of transmission characteristic, infrared rays of 1.3 μm wavelength were used so as to examine the initial characteristic and the temperature characteristic. Here, the term "initial characteristic" means the transmission characteristic at 20° C., and the term "temperature characteristic" means that the difference x |dB/km| between the transmission loss $x_0$ |dB/km| at 20° C. and the transmission loss $x_1$ |dB/km| at −40° C., that is, $x - x_1 - x_0$ |dB/km|.

COMPARATIVE EXAMPLE 1

Single mode (SM) preform was spun so as to be formed into a glass fiber having a fiber diameter of 125 μm, the glass fiber was coated with thermosetting silicone resin at a fiber speed of 200 m/minute, a then the coating was cured so that an optical fiber having a diameter of 200 μm was obtained. Then, nylon 12 was utilized so as to cover the optical fiber so that an optical transmission fiber having a diameter of 600 μm was obtained. Then, the characteristics of the final optical transmission fiber were estimated to obtain the result shown in FIG. 4. As the result of measurement, for estimating the transmission characteristics, lower limit of temperature at which the dynamic loss (tan δ) begins to indicate 0.05 in the temperature characteristic of the dynamic loss (tan δ), obtained was about 70° C. In the optical transmission fiber of the Comparative Example 1, the transmission loss was high, particularly at a low temperature.

COMPARATIVE EXAMPLE 2

SM preform was spun so as to be formed into a glass fiber having a fiber diameter of 125 μm, the glass fiber was coated with UV curable soft resin of urethane acrylate added with a silane coupling agent by 0.1% at a fiber speed of 200 m/minute, and then the coating was dried so that an optical fiber having a diameter of 190 μm was obtained. Succeedingly, the optical fiber was coated with UV curable hard resin of urethan acrylate at the same fiber speed and the coating was cured so as to obtain an optical transmission fiber having a diameter of 250 μm. Then, the characteristics of the thus obtained optical transmission fiber was estimated to obtain the result shown in FIG. 4. The lower limit of temperature at which the dynamic loss (tan δ) begins to indicate 0.05 measured for estimating the transmission characteristics, and obtained 65° C. and the transmission loss was high particularly at a low temperature.

COMPARATIVE EXAMPLE 3

Graded-Index (GI) preform was spun so as to be formed into a glass fiber having a fiber diameter of 125 μm, the glass fiber was coated with UV curable soft resin of urethane acrylate added with a silane coupling agent by 0.05% at a fiber speed of 200 m/minute, and then the coating was cured so that an optical fiber having a diameter of 200 μm was obtained. Succeedingly, nylon 12 was utilized so as to cover the optical fiber so that an optical transmission fiber having a diameter of 600 μm was obtained. Then, the characteristics of the thus obtained optical transmission fiber was estimated to obtain the result shown in FIG. 4. The lower limit of temperature at which the dynamic loss (tan δ) begins to indicate 0.05 measured for estimating the transmission characteristics, and obtained the transmission loss was high particularly at a low temperature.

EMBODIMENT 1

SM preform was spun so as to be formed into a glass fiber having a fiber diameter of 125 μm, the glass fiber was coated with thermosetting silicone resin at a fiber speed of 200 m/minute, and then the coating was cured so that an optical fiber having a diameter of 200 μm was obtained. The content of OH-radicals in the silicone resin was selected to be less than that in the Comparative Example 1 so as to weaken the tightness between the silicone resin and the glass fiber. Succeedingly, nylon 12 as utilized so as to cover the optical fiber so that an optical transmission fiber having a diameter of 600 μm was obtained. Then, the characteristics of the thus obtained optical transmission fiber was estimated so as to obtain the result shown in FIG. 4. As the result of measurement of the lower limit of temperature at which the dynamic loss (tan δ) begins to indicate 0.05 in the temperature characteristic of the dynamic loss (tan δ), obtained was about 40° C. In the optical transmission fiber of the Example 1, the transmission loss was low even at a low temperature and had a good transmission characteristic.

EMBODIMENT 2

SM preform was spun so as to be formed into a glass fiber having a fiber diameter of 125 μm, the glass fiber was coated with UV setting soft resin of urethane acrylate added with no silane coupling agent at a fiber speed of 200 m/minute, and then the coating was dried so that an optical fiber having a diameter of 190 μm was obtained. Succeedingly, the optical fiber was coated with UV curable hard resin of urethane acrylate at the same fiber speed and the coating was cured so as to obtain an optical transmission fiber having a diameter of 250 μm. Then the characteristics of the thus obtained optical transmission fiber was estimated to obtain the result shown in FIG. 4. The lower limit of temperature at which the dynamic loss (tan δ) begins to indicate 0.05 measured for estimating the transmission characteristics, and obtained 10° C. and showed a good transmission characteristic even at a lower temperature.

EMBODIMENT 3

GI preform was spun so as to be formed into a glass fiber having a fiber diameter of 125 μm, the glass fiber was coated with UV curable soft resin of urethane acrylate added with no silane coupling agent at a fiber speed of 200 m/minute, and then the coating was cured so that an optical fiber having a diameter of 200 μm was obtained. Succeedingly, nylon 12 was utilized so as to cover the optical fiber so that an optical transmission fiber having a diameter of 600 μm was obtained. Then, the characteristics of the thus obtained optical transmission fiber was estimated to obtain the result shown in FIG. 4. The lower limit of temperature at which the dynamic loss (tan δ) begins to indicate 0.05 measured for estimating the transmission characteristics, and obtained −18° C. and showed good transmission characteristic even at a low temperature.

The present invention is not limited to the above-mentioned examples but can be variously modified.

For example, the glass fiber may be formed of organic glass other than silica and fluoride glass. Further, the optical fiber is not limited to have such a structure having a single core but may have a structure having multi-cores.

The above-described embodiments employ a temperature at which the dynamic loss (tan δ) begins to indicate 0.05 as a basis for estimating the tightness. However, the invention is not limited thereto. For example, another temperature at which the dynamic loss (tan δ) is higher than 0.05 is the case where it is higher than 0.01 or lower than 0.07. Further, a temperature at which a curve of temperature of the dynamic loss (tan δ) indicates a peak value may be applicable. Furthermore, the above-described embodiments estimate the characteristics based upon the fact that whether the temperature at which the dynamic loss (tan δ) is higher than 60° C. or not. However, the invention is not limited thereto since an obtained data and a temperature dependency of the dynamic loss (tan δ) may vary when the chucks 7 and 8 of FIG. 1 are changed to other chucks of parallel plates or of V-groove. Further, the data and the temperature dependency may also vary according to a size of the chuck plane or whether the chuck contacts to an end of the glass fiber 1 or not.

In the plastic-coated optical transmission fiber and the estimating method thereof according to the present invention, microbending is never generated in the glass fiber over a wide temperature range, so that a superior transmission characteristic can accurately be estimated and realized.

What is claimed is:

1. An optical transmission line, comprising:
   a glass fiber; and
   a coating of an organic matter covering said class fiber, said glass fiber and said coating of said organic matter being in sufficiently close contact that the lower limit of temperature at which a dynamic loss (tan δ) begins to indicate 0.05 or more is not higher than 60° C. when dynamic viscoelasticity is measured in a manner so that dynamic vibrations are applied to one end and stress is detected at the other end of said optical-transmission fiber.

2. An optical transmission line according to claim 1, wherein said coating of an organic matter comprises:
   a soft layer closely contacting with said glass fiber; and
   a hard layer surrounding said soft layer.

3. An optical transmission line according to claim 2, wherein said soft layer is formed of thermosetting silicone resin and said hard layer is formed of polyamide resin.

4. An optical transmission line according to claim 1, wherein said coating of an organic matter is formed of ultraviolet-curable resin.

5. A method of measuring dynamic viscoelasticity for estimating the degree of tightness between glass fibers and coating materials in realizing the optical transmission fibers including
   cutting the optical transmission fiber into a fixed length and holding said length at one end by a vibration chuck and at the other end by a detection chuck, and
   detecting stress of optical transmission fibers through the arrangement of the chucks is possible and the measuring of the dynamic viscoelasticity on the basis of the detected stress so as to obtain a dynamic (loss (tan δ) is done.

* * * * *